(12) United States Patent
Ojosnegros Martos et al.

(10) Patent No.: US 10,213,282 B2
(45) Date of Patent: Feb. 26, 2019

(54) IN VITRO PLATFORM AND METHODS FOR CULTURING EMBRYOS FOR IMPLANTATION

(71) Applicant: CALIFORNIA INSTITUTE OF TECHNOLOGY, Pasadena, CA (US)

(72) Inventors: Samuel Ojosnegros Martos, Barcelona (ES); Carol Readhead, Pasadena, CA (US); Ayelet Lesman, Rehovot (IL)

(73) Assignee: California Institute of Technology, Pasadena, CA (US)

( * ) Notice: Subject to any disclaimer, the term of this patent is extended or adjusted under 35 U.S.C. 154(b) by 346 days.

(21) Appl. No.: 14/698,839

(22) Filed: Apr. 28, 2015

(65) Prior Publication Data

US 2015/0305774 A1    Oct. 29, 2015

Related U.S. Application Data

(60) Provisional application No. 61/985,214, filed on Apr. 28, 2014.

(51) Int. Cl.
*A61B 17/435*    (2006.01)
*A61D 19/04*     (2006.01)
*C12N 5/073*     (2010.01)

(52) U.S. Cl.
CPC ........... *A61D 19/04* (2013.01); *C12N 5/0604* (2013.01); *C12N 2533/54* (2013.01); *C12N 2533/56* (2013.01); *C12N 2537/10* (2013.01)

(58) Field of Classification Search
CPC .............. C12N 5/0604; C12N 2537/10; C12N 2533/54; C12N 2533/56; A61D 19/04
USPC ............................................. 600/34; 435/397
See application file for complete search history.

(56) References Cited

U.S. PATENT DOCUMENTS

| | | | |
|---|---|---|---|
| 2002/0088019 A1* | 7/2002 | Yacoby-Zeevi | A01K 67/0271 800/21 |
| 2005/0244970 A1* | 11/2005 | Zhang | C12N 5/0606 435/455 |
| 2015/0114310 A1* | 4/2015 | Hansen | A01K 29/005 119/712 |

FOREIGN PATENT DOCUMENTS

WO    WO 2013/001315 A1    1/2013

OTHER PUBLICATIONS

Kolehmainen, K., Willerth, S.M. Preparation of 3D Fibrin Scaffolds for Stem Cell Culture Applications. J. Vis. Exp. (61), e3641, DOI :10.3791/3641 (2012)., pp. 1-4.*
W. Matthew Petroll,Differential Interference Contrast and Confocal Reflectance Imaging of Collagen Organization in Three-Dimensional Matrices, Scanning vol. 28, 305-310 (2006).*
Chemicon International, 3D Collagen Cell Culture System (Cat. No. ECM 675), Feb. 2002, Revision B: 41265.*

(Continued)

*Primary Examiner* — Navin Natnithithadha
*Assistant Examiner* — Sunita Reddy
(74) *Attorney, Agent, or Firm* — Lewis Roce Rothgerber Christie LLC

(57) ABSTRACT

A mammalian in vitro system for culturing an embryo includes a collagen or fibrin matrix and endometrial and/or stromal cells. The in vitro platforms and methods according to embodiments of the invention allow for in vitro embryonic development (including implantation) prior to transfer of the embryo complex in vivo for further development.

13 Claims, 11 Drawing Sheets
(8 of 11 Drawing Sheet(s) Filed in Color)

(56) References Cited

OTHER PUBLICATIONS

Abrahamsohn, Paulo A. et al. "Implantation and Decidualization in Rodents"; The Journal of Experimental Zoology; 266; 1993; pp. 603-628.

Bermejo-Alvarez, P. et al.; "Utero-tubal embryo transfer and vasectomy in the mouse model"; J. Vis. Exp.; Feb. 28, 2014; 84; e51214, 8pp.

Carbone, Karin et al.; "Arrangement and Fine Structure of Collagen Fibrils in the Decidualized Mouse Endometrium"; Microscopy Research and Technique; 69; 2006; pp. 36-45.

Cui, Lifang et al.; "Transcervical embryo transfer in mice"; J. Am. Assoc. Lab. Anim. Sci.; vol. 53; No. 3; May 2014; pp. 228-231.

Dai, Wangde et al.; "Thickening of the Infarcted Wall by Collagen Injection Improves Left Ventricular Function in Rats: A Novel Approach to Preserve Cardiac Function After Myocardial Infarction"; Journal of the American College of Cardiology; vol. 46; No. 4; Aug. 16, 2005; pp. 714-719.

Healy, M.W. et al.; "Optimal oocyte retrieval and embryo transfer techniques: where we are and how we got here"; Seminars in Reproductive Medicine; vol. 33; No. 2; Mar. 2015; pp. 83-91.

Drury, Jeanie L. et al.; "Hydrogels for tissue engineering: scaffold design variables and applications"; Biomaterials; vol. 24; Issue 24; Nov. 2003; pp. 4337-4351.

Lesman, Ayelet et al.; "Engineering vessel-like networks within multicellular fibrin-based constructs"; Biomaterials; 2011; 14pp.

Muzumdar, Mandar Deepak et al.; "A global double-fluorescent Cre reporter mouse"; Genesis; vol. 45; Issue 9; Sep. 2007; pp. 593-605.

Porter, Misty Blanchette; "Ultrasound in Assisted Reproductive Technology"; Seminars in Reproductive Medicine; vol. 26; No. 3; 2008; pp. 266-276.

Sheu, Ming-Thau et al.; "Characterization of collagen gel solutions and collagen matrices for cell culture"; Biomaterials; 22; 2001; pp. 1713-1719.

Silva, Raquel et al.; "Fibrous protein-based hydrogels for cell encapsulation"; Biomaterials; vol. 35; Issue 25; Aug. 2014; pp. 6727-6738.

Spiess, Karin et al.; "Collagen Types I, III, and V Constitute the Thick Collagen Fibrils of the Mouse Decidua"; Microscopy Research and Technique; 70; 2007; pp. 18-25.

Spiess, Karin et al.; "Distribution of Collagen Types I, III, and V in Pregnant Mouse Endrometrium"; Connective Tissue Research; 48; 2007; pp. 99-108.

Tan, Huaping et al.; "Injectable In Situ Forming Biodegradable Chitosan-Hyaluronic acid Based Hydrogels for Cartilage Tissue Engineering"; Biomaterials; 30(13); May 2009; pp. 2499-2506.

Teklenburg, Gijs et al.; "Natural Selection of Human Embryos: Decidualizing Endometrial Stromal Cells Serve as Sensors of Embryo Quality upon Implantation"; PLoS ONE; Apr. 2010; vol. 5; Issue 4; 6pp.

Zhu, Junmin; "Bioactive Modification of Poly(ethylene glycol) Hydrogels for Tissue Engineering"; Biomaterials; 31(17); Jun. 2010; pp. 4639-4656 (42pp).

* cited by examiner

IN VITRO PLATFORM AND METHODS FOR CULTURING EMBRYOS FOR IMPLANTATION

CROSS-REFERENCE TO RELATED APPLICATION(S)

The present application claims priority to and the benefit of U.S. Provisional Application Ser. No. 61/985,214 filed on Apr. 28, 2014, the entire contents of which are incorporated herein by reference.

BACKGROUND

The implantation of mammalian embryos at the blastocysts stage is crucial for the normal development of the embryo. Impaired implantation and subsequent formation of the placenta in early pregnancy is thought to be the leading cause of preeclampsia that causes fetal and neonatal morbidity and mortality and can lead to an increased risk of cardiovascular disease. This complex implantation process involves the blastocyst's apposition to the uterine epithelium, its attachment, followed by its subsequent invasion of the uterine epithelium and interaction with the stroma cells of the uterus and finally the establishment of the placenta.

In vitro fertilization (IVF) of human eggs is a technique that involves the fertilization of eggs harvested from the uterus and the subsequent transfer of the fertilized eggs (embryos) to the uterus that will continue to develop the embryo. IVF has resulted in millions of babies born to couples who were previously infertile. This technology is practiced in fertility clinics around the world and though its efficiency has improved, it is still not highly efficient. According to the American pregnancy association (http://americanpregnancy.org/corp-sponsors/fairhaven-healthImplantation) the number of live births from IVF is 30-35% for women under 35, but drops to 6-10% in women over 40. The reason for this is a combination of the quality of the embryo that has been fertilized in vitro and its ability to implant and thrive in the uterus of the mother.

Current IVF protocols include the culturing of human embryos in the laboratory until the embryo reaches the blastocyst stage. However only a small subset of the blastocysts transferred to the mother actually implant and develop further. Most of the blastocysts fail to attach properly to the uterus and are essentially lost after the transference. As such, in order to obtain a higher pregnancy rate per IVF cycle, it is currently conventional practice to transfer multiple embryos to the mother. This procedure has the undesirable effect of rendering multiple pregnancies (IVF twins, triplets etc.) in many occasions and the associated health cost of multiple pregnancies. According to the CDC (http://www.cdc.gov/art/preparingforart/eset.htm), multiple births increase the risk of premature birth and low birth weight in infants. There is therefore a desire to find a more effective and efficient IVF technique that facilitates the implantation of the embryo to the mother uterus, thereby reducing the number of embryos transferred to the mother per cycle.

SUMMARY

In some embodiments of the present invention a method is provided for the in vitro culturing of a mammalian embryo derived from a first uterus for implantation into a second uterus. The first uterus may be the same or different from the second uterus. The method includes harvesting endometrial cells from the first uterus, adding the harvested endometrial cells to a collagen or fibrin matrix forming an endometrial-collagen matrix or an endometrial-fibrin matrix, and adding an isolated embryo to the endometrial-collagen matrix or the endometrial-fibrin matrix to form an in vitro embryo culture complex.

In some embodiments of the present invention, a method is provided for the in vitro culturing of a mammalian embryo derived from a first uterus for implantation into a second uterus. The first uterus may be the same or different from the second uterus. The method includes harvesting stromal cells from the first uterus, adding the harvested stromal cells to a collagen or fibrinogen suspension to form a stromal-collagen or stromal-fibrinogen suspension, polymerizing the stromal-collagen or stromal-fibrinogen suspension to form a stromal-collagen matrix or a stromal-fibrin matrix, and adding an isolated embryo to the stromal-collagen matrix or the stromal-fibrin matrix to form an in vitro embryo culture complex.

In some embodiments of the present invention, a method is provided for the in vitro culturing of an embryo derived from a first uterus for implantation into a second uterus. The first uterus may be the same or different from the second uterus. The method includes adding endometrial cells and/or stromal cells from the first uterus to a collagen suspension or a fibrinogen suspension to form a cell-collagen suspension or a cell-fibrinogen suspension, adding an isolated embryo derived from a first uterus to the cell-collagen or cell-fibrinogen suspension to form an embryo-collagen suspension or an embryo-fibrinogen suspension, and polymerizing the cell-embryo-collagen suspension or the cell-embryo-fibrinogen suspension to form a cell-embryo-collagen complex or a cell-embryo-fibrin complex.

In some embodiments of the present invention, a mammalian in vitro system is provided for culturing an embryo derived from a first uterus for implantation into a second uterus. The first uterus may be the same or different from the second uterus. The system includes endometrial cells harvested from the first uterus, and a collagen or fibrin matrix including the harvested endometrial cells. In some embodiments, the system also includes stromal cells. In some embodiments, the system also includes an isolated embryo.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

DETAILED DESCRIPTION

Figure 1:
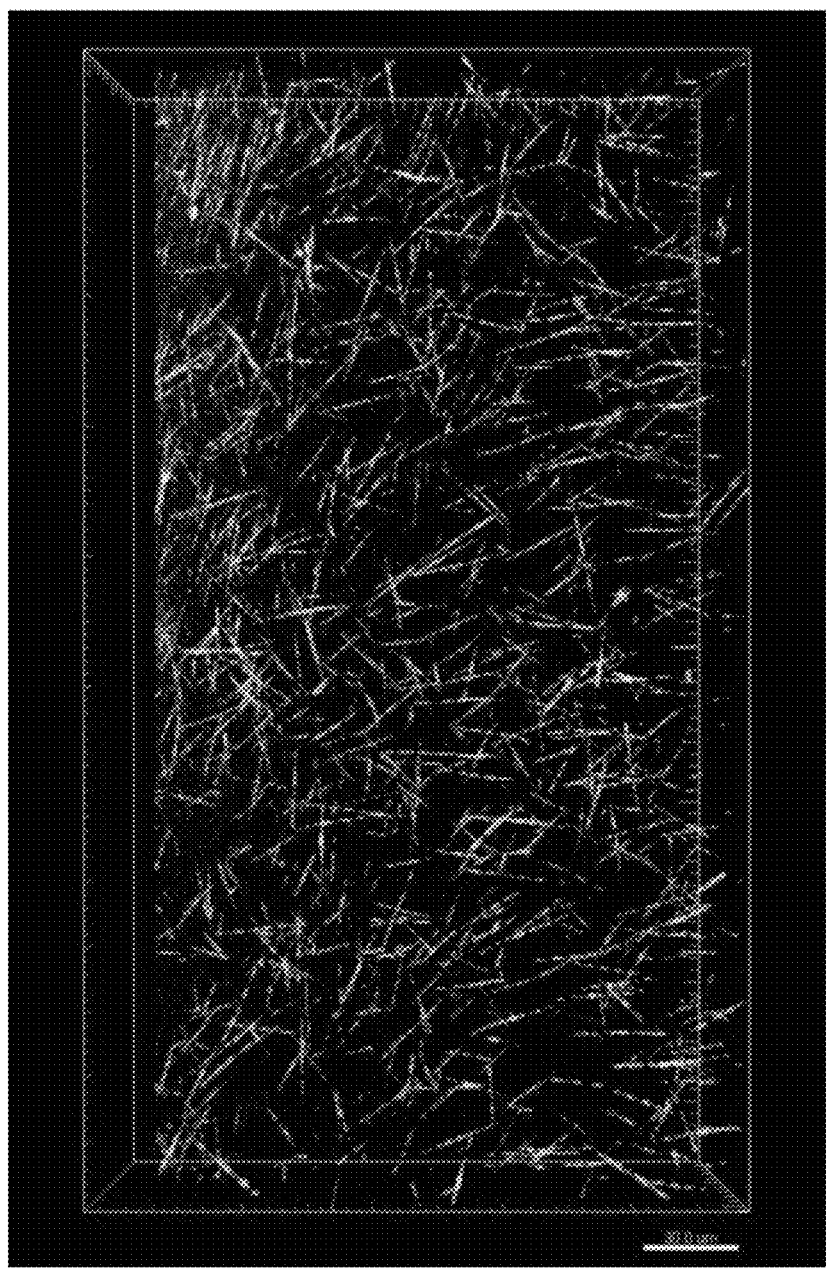
FIG. 1 is an image from a reflection microscope of polymerized collagen fibers (shown in white) in a matrix, according to embodiments of the present invention.

Mammalian embryonic implantation is a complex process involving interactions between the embryo and the cells of the uterus requiring differentiation of the uterine cells in order to respond to the embryo. According to aspects of embodiments of the present invention, culturing systems and methods provide for in vitro culturing and implantation of the embryo. The systems and methods according to embodiments of the present invention include harvested cells from the uterus that donates the embryo together with a collagen or fibrin matrix, thereby creating an in vitro environment for the initial development, hatching, (from the zona pellucida (ZP)) and implantation of the embryo outside of the uterus. The systems and methods according to embodiments of the present invention enable monitored growth as well as the studying and imaging of early embryogenesis (e.g., hatching and implantation) in vitro. In this way, the systems and methods according to embodiments of the present invention provide a controlled and accessible system that allows the embryo to accomplish the complex process of implanting in vitro followed by the transfer of the "pre-implanted" embryo-matrix complex into a uterus for continued development in vivo.

As used herein, the term "embryo," "embryonic," and like terms refer to a fertilized egg cell that has undergone mitosis to produce a multicellular diploid. Embryos as used herein refer to mammalian embryos. "Isolated embryo" refers to an embryo outside of a uterus.

As used herein, the term "blastocyst" refers to an embryo at mammalian embryological Stage 2, 3, or 4, as defined by the Carnegie Stages based on the external and/or internal morphological development of the embryo, and are not directly dependent on age or size. The Carnegie stages may be applied to any mammalian species.

As used herein, the term "collagen" and like terms, unless stated otherwise, refer to all types of collagen in the form of soluble collagen and insoluble collagen. "Soluble collagen" refers to purified soluble collagen of any type. Polymerized soluble collagen is also referred to as a collagen gel. "Insoluble collagen" refers to crosslinked collagen of any type in which the crosslinking renders the collagen in a solid form. A solid form of insoluble collagen may take the form of a sheet or membrane.

As used herein "endometrial," "endometrial cells," "endometrium," and like terms refer to the epithelial cell layer that covers the lumen of the mammalian uterus.

As used herein, "stromal," "stromal cells," and like terms refer to the cells found in the decidua tissue in the uterus. The decidua tissue includes a mix of stromal and fibroblast cells in a ratio of approximately 80% stromal cells and 20% fibroblast cells. The decidua is located underneath and adjacent to the endometrium of the uterus.

As used herein, "matrix," "matrices," and like terms refer to a scaffold made of collagen or fibrin. The matrix may also include uterine cells (e.g., endometrial and/or stromal cells) either polymerized within the scaffold and/or layered on top of the matrix. The "top of the matrix," refers to the exposed side of the matrix opposite the side of the matrix that is in contact with a substrate (e.g., a culturing dish).

As used herein a three dimensional (3D) matrix ("3D matrix") refers to a collagen or fibrin matrix that is polymerized with the embryo in a pre-polymerized suspension.

As used herein, a two-dimensional (2D) matrix ("2D matrix") refers to a collagen or fibrin matrix that is polymerized to form a gel or crosslinked to form a membrane prior to the addition of the embryo to be cultured thereon.

As used herein, "complex" and like terms refer to a matrix as defined herein, in combination with an embryo. The entire complex is also referred to interchangeably as a "platform." As used herein a "stromal-collagen-embryo" complex, and similar terms does not assign any order to the components (stromal, collagen, and embryo), and is interchangeable with, for example, embryo-stromal-collagen.

As used herein, "hatching," "hatched," and like terms refer to an embryo that has separated from, or is separating from, the zona pellucida (ZP). The ZP is the egg coat surrounding a mammalian oocyte.

As used herein, the term "implantation" refers to the attachment of the embryo to the uterine wall in vivo or attachment of an isolated embryo to a uterine cell matrix in vitro. Attachment in vitro and in vivo may be referred to as "implantation," whereas "pre-implantation" as used herein, refers to attachment of the embryo in vitro, e.g., to a uterine cell matrix.

As used herein, "a first uterus," and like terms refers to the uterus from which the embryo is derived. The embryo is not necessarily isolated directly from the first uterus, as the embryo may result from in vitro fertilization of an egg cell isolated from the first uterus. In this way, the embryo is derived from the first uterus.

As used herein, "a second uterus," and like terms refers to the uterus to be implanted with the cultured embryo. As will be understood by a person skilled in the art, the first uterus and the second uterus may be the same uterus or may be different uteri. In the case of a surrogate pregnancy, the first uterus donates the egg, and the second uterus carries the embryo to birth.

Collagen/Fibrin Matrices

According to embodiments of the present invention, a collagen or fibrin matrix is utilized as a scaffold support for culturing embryos in vitro. In some embodiments of the present invention, a collagen or fibrin matrix together with uterine cells and supplemented growth media produce an in vitro culturing system for early embryo development.

White fibers of a collagen gel matrix are shown in FIG. 1. Implantation of an isolated embryo into the collagen or fibrin matrix is visualized by the aggregation of the white collagen or fibrin fibers.

In some embodiments of the present invention, collagen matrices are prepared by the polymerization of soluble collagen to form a collagen gel or the use of insoluble (crosslinked) collagen sheets or membranes. For collagen matrices made from polymerized soluble collagen, any type of purified collagen may be used. Type I, III, and V collagens are expressed in the mammalian uterus. (See, e.g., Carbone et al., 2006, *Microscopy Research and Technique,* 69:36-45; Spiess and Zorn, 2007, *Microscopy Research and Technique,* 70:18-25; and Spiess et al., 2007, *Connective Tissue Research,* 48:99-108, the entire contents of all of which are herein incorporated by reference.) However, all types of collagen may be utilized as a suitable support matrix. In some embodiments, Type I, III, IV, and V collagen are used and may be used alone or in any combination. In some embodiments of the present invention, the collagen is purified from the same mammalian species as the embryo and uterus. For example, for in vitro culturing of a human embryo, purified human collagen may be utilized. Purified collagen may be purchased from any suitable supplier (e.g., VitroCol® from Advanced BioMatrix). Alternatively, collagen may be purified using established methods. Collagen spontaneously polymerizes at 37° C. in neutral pH. As such, a purified suspension of soluble collagen may be stored at 4° C. in a suitable buffer until it is ready for use. In some embodiments, polymerization of the collagen at 37° C. (in the presence or absence of cells and/or embryos) may be carried out for at least about 30 minutes to allow for the matrix to form.

Collagen matrices may also be made from insoluble collagen sheets or membranes. These crosslinked sheets are described, for example, in Sheu et al. 2001, *Biomaterials,* 22:171-1719, the entire content of which is herein incorporated by reference. For example, the collagen sheet is made of collagen solution (1-3%) treated with a crosslinker. Any suitable crosslinker may be used. Examples of crosslinkers include enzymatic crosslinkers and chemical crosslinkers. Non-limiting examples of crosslinkers include glutaraldehyde and diphenylphosphoryl azide. In some embodiments glutaraldehyde (0-0.2%) is used, and then the crosslinked collagen membrane is allowed to air dry or is dried with a freeze-dryer. The mechanical strength of the membrane may be controlled by the initial concentration of the collagen and by changing the concentration of the crosslinker.

Fibrin matrices may be made by polymerizing purified fibrinogen with thrombin at 37° C. In some embodiments, the fibrinogen is purified from the same mammalian species as the embryo and uterus. For example, for in vitro culturing of a human embryo, purified human fibrinogen 1, 2 and/or 3 may be utilized along with human thrombin to form human fibrin. Purified fibrinogen may be purchased from any suitable supplier (e.g., Human Fibrinogen 1, 2 or 3 from Enzyme Research Laboratories), or fibrinogen may be purified using established methods. Fibrinogen polymerizes to fibrin in the presence of thrombin at 37° C. As such, a purified suspension of soluble fibrinogen may be stored at 4° C. in a suitable buffer until it is ready for use. In some embodiments, polymerization of the fibrin at 37° C. (in the presence or absence of cells and/or embryos) is carried out for at least about 30 minutes to allow for the matrix to form.

Two-dimensional (2D) Matrix

In some embodiments of the present invention, a collagen or fibrin matrix is polymerized to form a collagen gel or fibrin gel in a culture dish with culturing of an isolated embryo on top of the matrix. In some embodiments, endometrial cells harvested from the uterus of the donor egg or donor embryo are added on top of a collagen gel or fibrin gel to form an endometrial-collagen matrix or an endometrial-fibrin matrix, respectively. In some embodiments, an endometrial-collagen matrix has a ratio of about 5 to 200 μg of collagen to about 10,000 to 200,000 endometrial cells. In some embodiments, an endometrial-fibrin matrix has a ratio of about 10 to 150 μg of fibrinogen to about 10,000 to 200,000 endometrial cells. In some embodiments, a suitable culture dish includes a 96-well culture plate.

Figure 2:
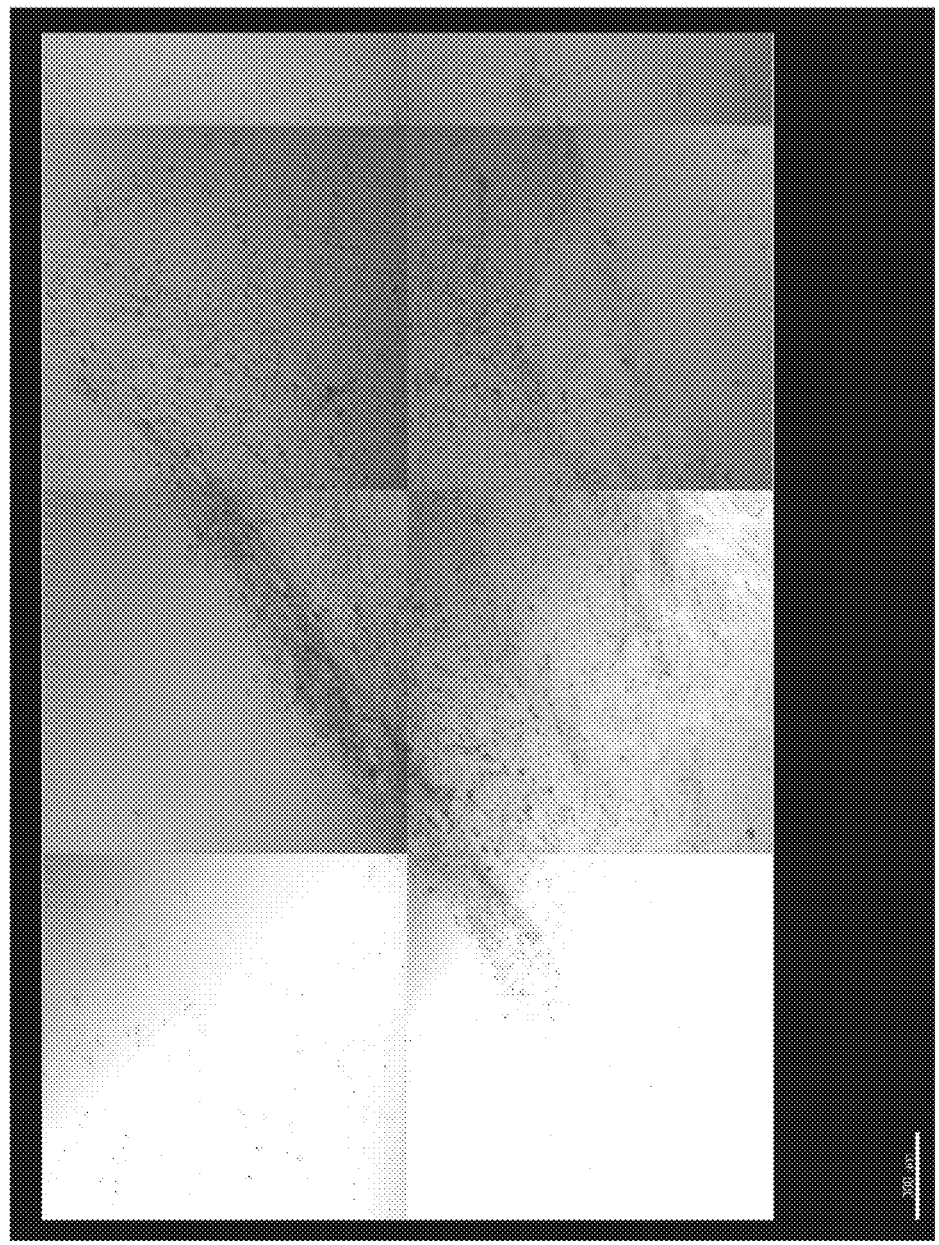
FIG. 2 is a two-dimensional (2D) differential interference contrast (DIC) image of stromal cells embedded in a collagen matrix, forming a stromal-collagen complex, according to embodiments of the present invention.
Figure 3:
FIG. 3 is a 2D DIC image of stromal cells embedded in a fibrin matrix, forming a stromal-collagen fibrin matrix, according to embodiments of the present invention.

In some embodiments of the present invention, stromal cells harvested from the uterus of the donor egg or donor embryo are mixed with a collagen suspension or fibrinogen suspension and the stromal cells are polymerized in a culture dish with the collagen or fibrin to form a stromal-collagen gel matrix or a stromal-fibrin gel matrix. In some embodiments, a stromal-collagen suspension includes about 10,000 to 200,000 stromal cells resuspended in a suitable buffer with 5 to 20 μg of collagen which is then polymerized at 37° C. to form a stromal-collagen matrix. A stromal-collagen matrix according to embodiments of the present invention is shown in FIG. 2. In some embodiments, a stromal-fibrinogen suspension includes 10,000 to 200,000 stromal cells resuspended in 5 to 20 μl of a 1 to 20 U/ml thrombin solution in a suitable buffer and then combined with 10 to 150 μg of fibrinogen and polymerized at 37° C. to form a stromal-fibrin matrix. A stromal-fibrin matrix according to embodiments of the present invention is shown in FIG. 3.

In some embodiments of the present invention, endometrial cells from the uterus of the donor egg or donor embryo are added on top of the stromal-collagen or stromal-fibrin matrix. In some embodiments 10,000-200,000 endometrial cells are resuspended in a medium and added to the top of the stromal-collagen or stromal-fibrin matrix.

Isolated embryos (at Stage 2, 3, or 4) may be placed on top of any of the collagen or fibrin matrices described above, thereby forming a 2D in vitro complex. A medium supplemented with serum is then added to cover the complex. After the embryo hatches from the zona pellucida (ZP), the embryo attaches to the endometrial cells, thereby implanting the embryo into the matrix.

In some embodiments of the present invention, a collagen gel or fibrin gel is polymerized on top of polyacrylamide. In this way, the polyacrylamide provides a stiffness that improves the handling of the culture and the collagen or fibrin provides a physiologically desired environment for the embryo.

Three-dimensional (3D) Matrix

In some embodiments of the present invention, a collagen or fibrin matrix is polymerized together with an isolated embryo to form a 3D matrix within which the embryo is embedded and cultured.

In some embodiments, a 3D collagen matrix is made from a collagen suspension added to a culture dish, followed immediately by the insertion of an isolated embryo (at Stage 2, 3, or 4) into the center of the suspension prior to polymerization of the collagen. After the matrix has polymerized to form a gel at 37° C., with the embryo embedded therein, a medium supplemented with serum is added to the culture dish to cover the collagen-embryo complex.

Figure 4:
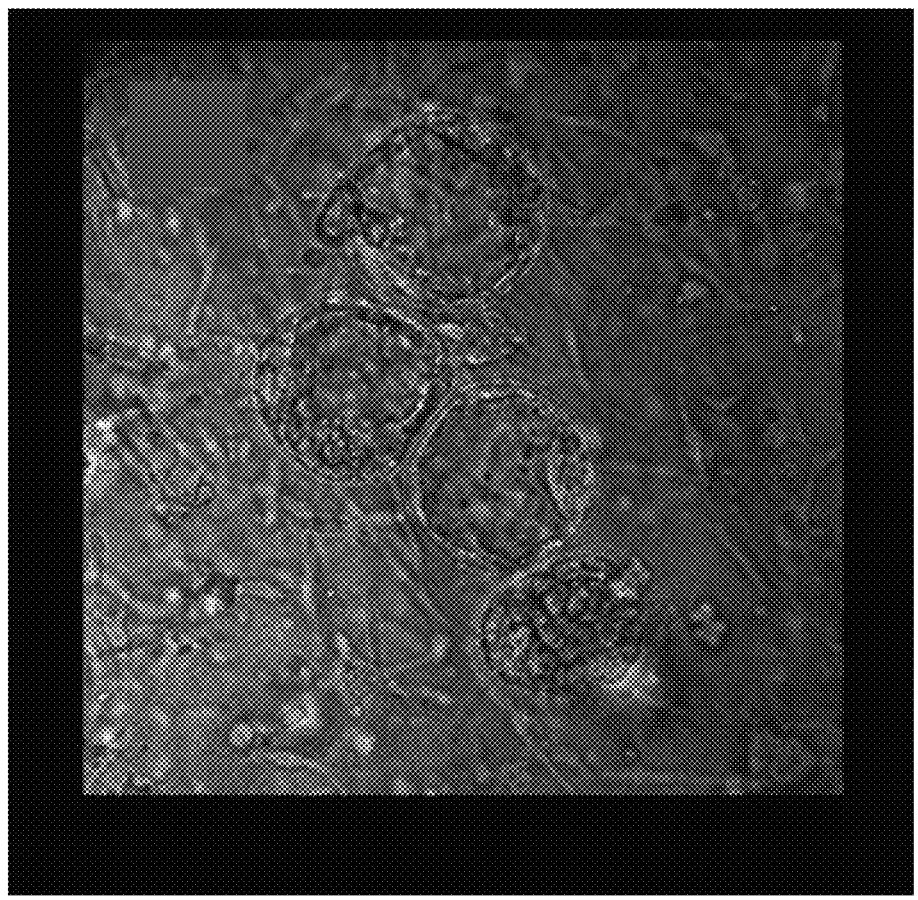
FIG. 4 is a 2D DIC image of a 3D stromal-collagen complex with four mouse blastocysts obtained from strain Gt(ROSA)26Sor$^{tm4(ACTB-tdTomato,-EGFP)luo}$/J, according to embodiments of the present invention.

In some embodiments, stromal cells and/or endometrial cells harvested from the uterus of the donor egg or donor embryo are added to the collagen suspension to form a stromal-collagen suspension, endometrial-collagen suspension, or endometrial-stromal-collagen suspension. These collagen suspensions may be kept cool to avoid premature polymerization of the collagen. These suspensions may be plated in a culture dish immediately followed by the insertion of an isolated Stage 2, 3, or 4 embryo into the center of the suspension, followed by polymerization of the collagen at 37° C. to form a stromal-collagen, endometrial-collagen or endometrial-stromal-collagen 3D in vitro embryo complex. A stromal-collagen 3D embryo complex according to embodiments of the present invention is shown in FIG. 4.

In some embodiments, a 3D fibrin matrix is made from a fibrinogen suspension added to a culture dish together with thrombin in suspension. Once the thrombin is added, an isolated embryo may be immediately added to the center of the suspensions. In some embodiments, the embryo is added to the fibrinogen and thrombin suspensions within 1 minute of the addition of thrombin to the fibrinogen. The fibrinogen/thrombin and embryo may then be incubated to complete the polymerization of the fibrin gel and the embryo is thereby embedded in the fibrin gel.

In some embodiments, stromal cells and/or endometrial cells harvested from the uterus of the donor egg or donor embryo are added to the fibrinogen suspension to form a stromal-fibrinogen suspension, endometrial-fibrinogen suspension, or endometrial-stromal-fibrinogen suspension. These fibrinogen suspensions are plated in a culture dish together with thrombin. Immediately following the addition of thrombin to the fibrinogen suspension, an isolated Stage 2, 3, or 4 embryo may be placed into the center of the suspension. The embryo and fibrinogen/thrombin and cell suspensions may then be allowed to completely polymerize at 37° C. forming an stromal and/or endometrial-fibrin embryo 3D complex.

After polymerization of the collagen or fibrin gels with endometrial and/or stromal cells and an embedded embryo, growth medium supplemented with serum is added to the culture dish to cover the in vitro complex and the embryo may then be cultured for further development and growth.

In some embodiments of the present invention, the collagen or fibrin matrices including the uterine cells may be prepared in combination with other suitable biomaterials. Suitable biomaterials include synthetic materials and naturally derived polymers. Non-limiting examples of synthetic materials include poly(ethylene oxide) (PEO), poly(vinyl alcohol) (PVA), poly(acrylic acid) (PAA), polypropylene furmarate-co-ethylene glycol) (P(PF-co-EG)), and polypeptides. Non-limiting examples of naturally derived polymers include agarose, alginate, chitosan, gelatin, and hyaluronic acid (HA). (See, e.g., Jeanie et al., 2003, *Biomaterial*, 24:4337-4351, the entire contents of which are herein incorporated by reference.)

In some embodiments of the present invention, suitable biomaterials that may be combined with the collagen or fibrin matrices of the present invention include Matrigel, Poly-1-lactic acid (PLA), polylactic-co-glycolic acid (PLGA) sponge and their combination, laminin, polyethylene glycol (PEG) alone and in combination with a natural protein or peptide (e.g. PEG-fibrinogen or PEG-RGD), chitosan-hyaluronic acid based hydrogels, silk, keratin elastin and resilin proteins. See, e.g., Lesman et al., 2011, *Biomaterials*, doi:10.1016/j.biomaterials.2011.07.003, Zhu 2010, *Biomaterials*, 31:4639-4656, Tan et al., 2009, *Biomaterials*, 30:2499-2506, and Silva et al., 2014, *Biomaterials*, 35:6727-6738, the entire contents of all of which are herein incorporated by reference.

Observation of Embryogenesis In Vitro

Figure 5:
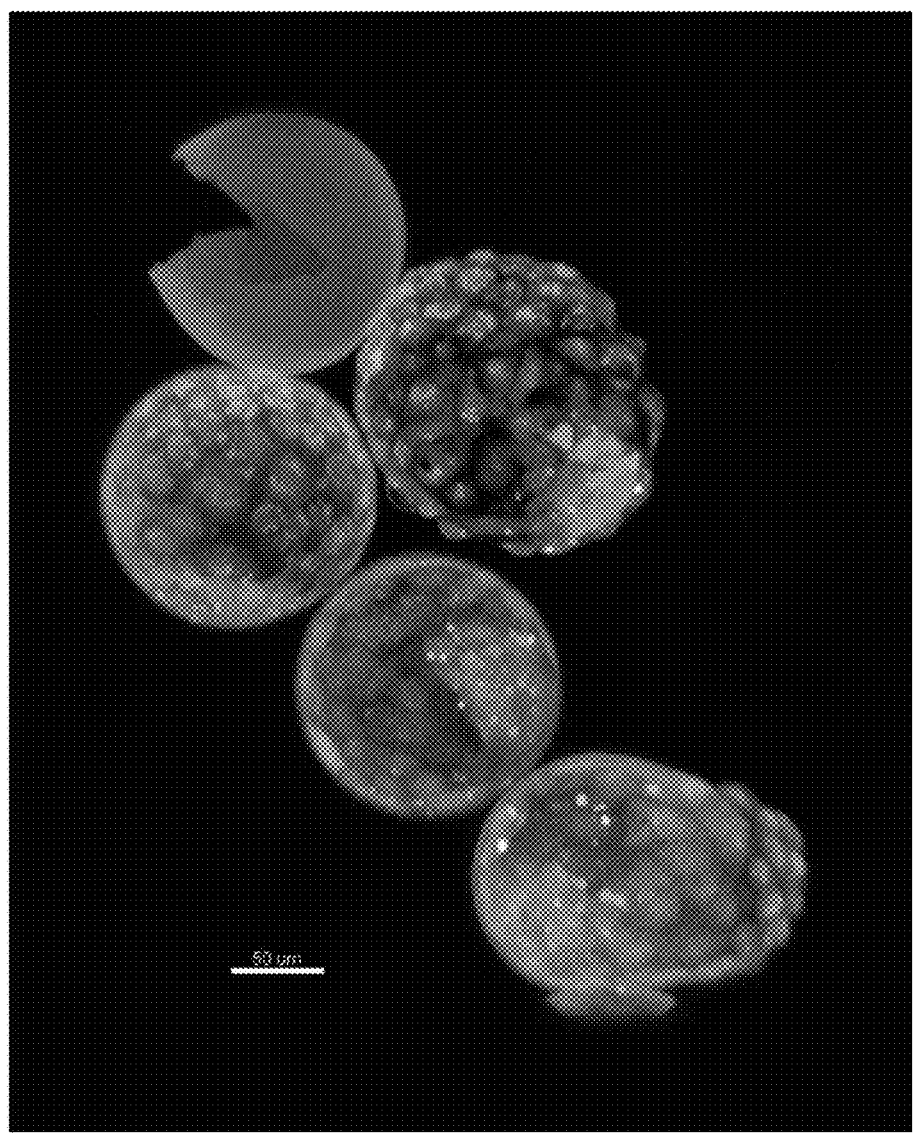
FIG. 5 is an image produced from a 3D reconstruction using fluorescent confocal imaging, showing mouse blastocyst morphology of embryos obtained from an Oct4-GFP transgenic mouse strain, in which the zona pellucida (ZP) was stained using an Alexa 647 conjugated lectin as shown in purple; the two embryos in the center are inside the ZP, the bottom embryo is just starting to hatch from the ZP, and the top one has hatched from the ZP, according to embodiments of the present invention.

In some embodiments of the present invention, as the embryo (blastocyst) grows in the 2D or 3D collagen or fibrin complex (in the presence of endometrial cells and/or stromal cells), some stages of embryogenesis may be observed. For example, hatching of the embryo from the zona pellucida (ZP) is observed in FIG. 5.

Previous studies using collagen matrices during embryo implantation have used fixed tissue slices since the process takes place inside the uterus and is not accessible to imaging. Thus, details on the process of embryo implantation are not complete. Using in vitro systems and methods according to embodiments of the present invention allows for the monitoring of the implantation process including embryo shape changes over time, the development of the polarity axis, as well as embryo-matrix interactions.

Figure 6A:
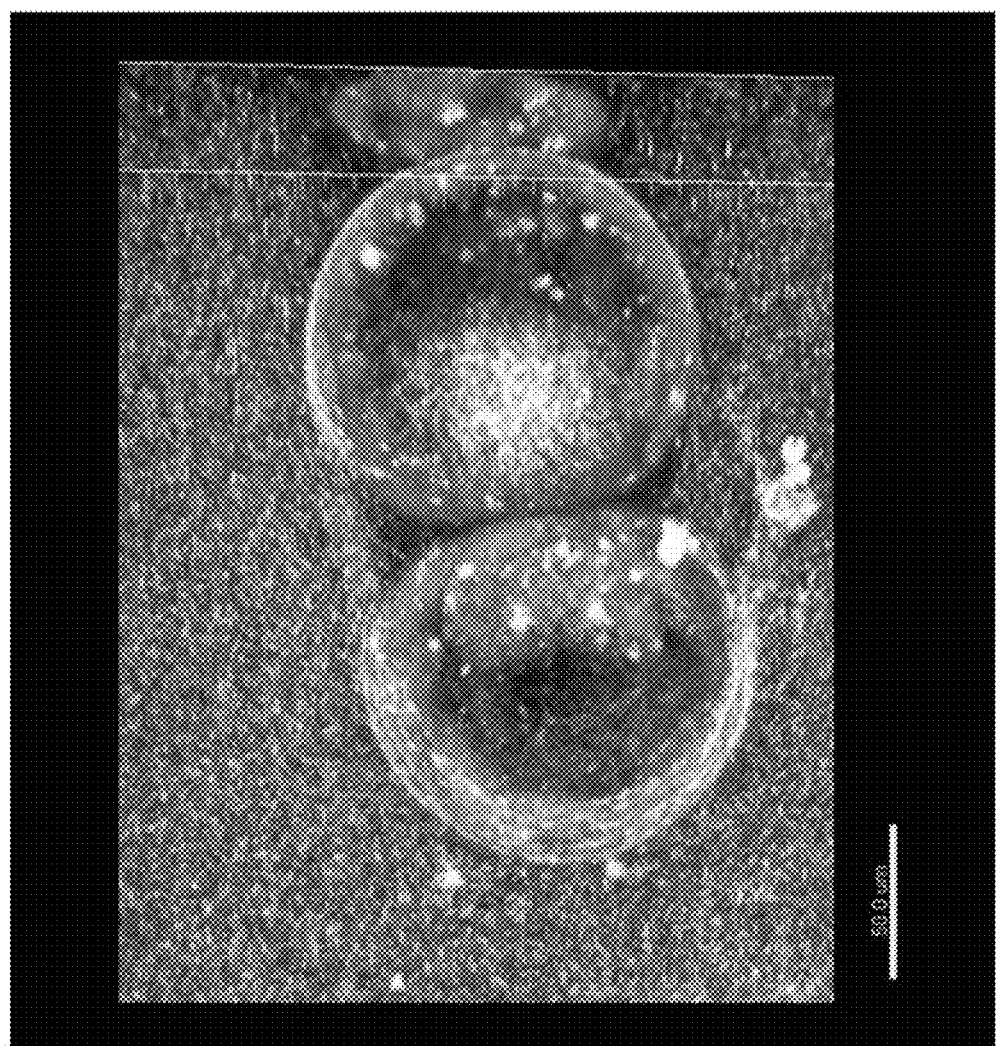
FIG. 6A is a 3D confocal reconstruction image of two Oct4-GFP mouse embryos embedded in a 3D stroma-collagen-endometrial matrix before hatching from the ZP, in which the collagen is shown as white, the embryo cells are green, and the ZP is stained with Alexa647-lectin (purple), according to embodiments of the present invention.
Figure 6B:
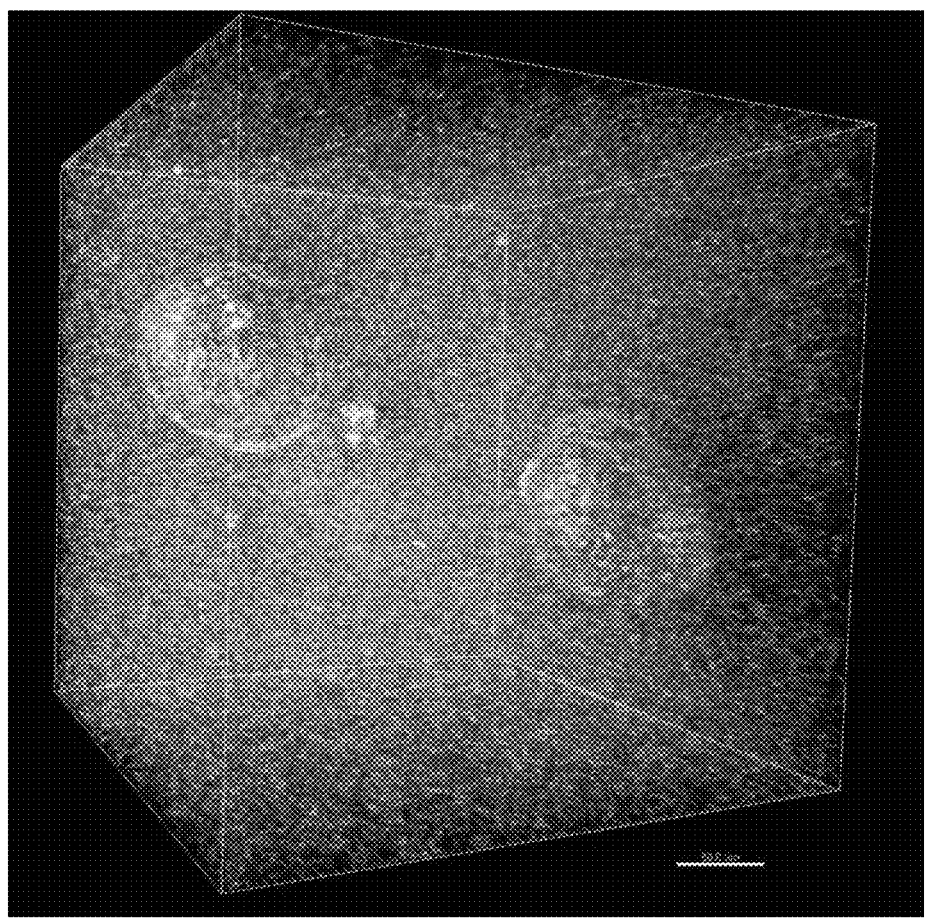
FIG. 6B is a 3D confocal reconstruction image of three (upper left, back center and middle right) Oct4-GFP mouse embryos embedded in a 3D stroma-collagen-endometrial matrix each of the embryos shown has hatched from the ZP, in which the collagen is shown as white and the embryo cells are green, according to embodiments of the present invention.

FIG. 6A is a confocal reconstruction image of mouse embryos from Oct4-GFP (green fluorescent protein) transgenic mouse embedded in a 3D stroma-collagen endometrial complex, in which the collagen is shown in white, the ZP is stained purple with Alexa647-lectin stain, and the green embryonic cells show that the embryo is still inside the ZP. FIG. 6B is a confocal reconstruction image of Oct4-GFP mouse embryos embedded in a 3D stromal-collagen-endometrial gel in which the green fluorescent embryos are shown at various stages of hatching from the ZP.

Figure 6C:
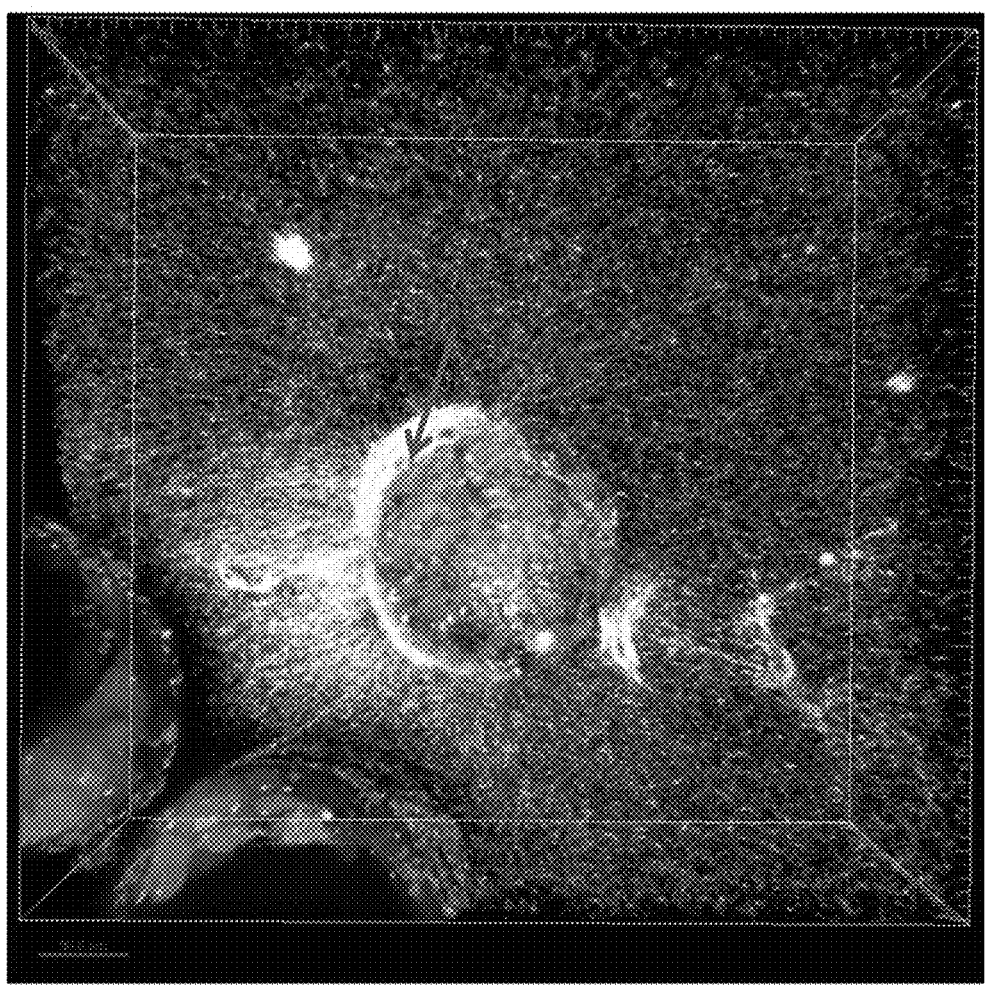
FIG. 6C is a 3D confocal reconstruction image of an Oct4-GFP mouse embryo embedded in a 3D stroma-collagen-endometrial matrix in which the embryo has hatched and implanted in the stroma-collagen-endometrial matrix, as indicated by the "pulled" collagen fibers (white); the red arrow points to the where the collagen fibers are more dense and aligned towards the embryo indicating that the embryo is pulling the matrix, according to embodiments of the present invention.

FIG. 6C is a confocal reconstruction image of Oct4-GFP mouse embryos embedded in a 3D stroma-collagen-endometrial gel matrix in which the green fluorescent embryos have hatched from the ZP and are implanted in the gel matrix as indicated by the "pulled" collagen white fibers which are shown to be have aligned in a more dense white pattern.

Figure 6D:
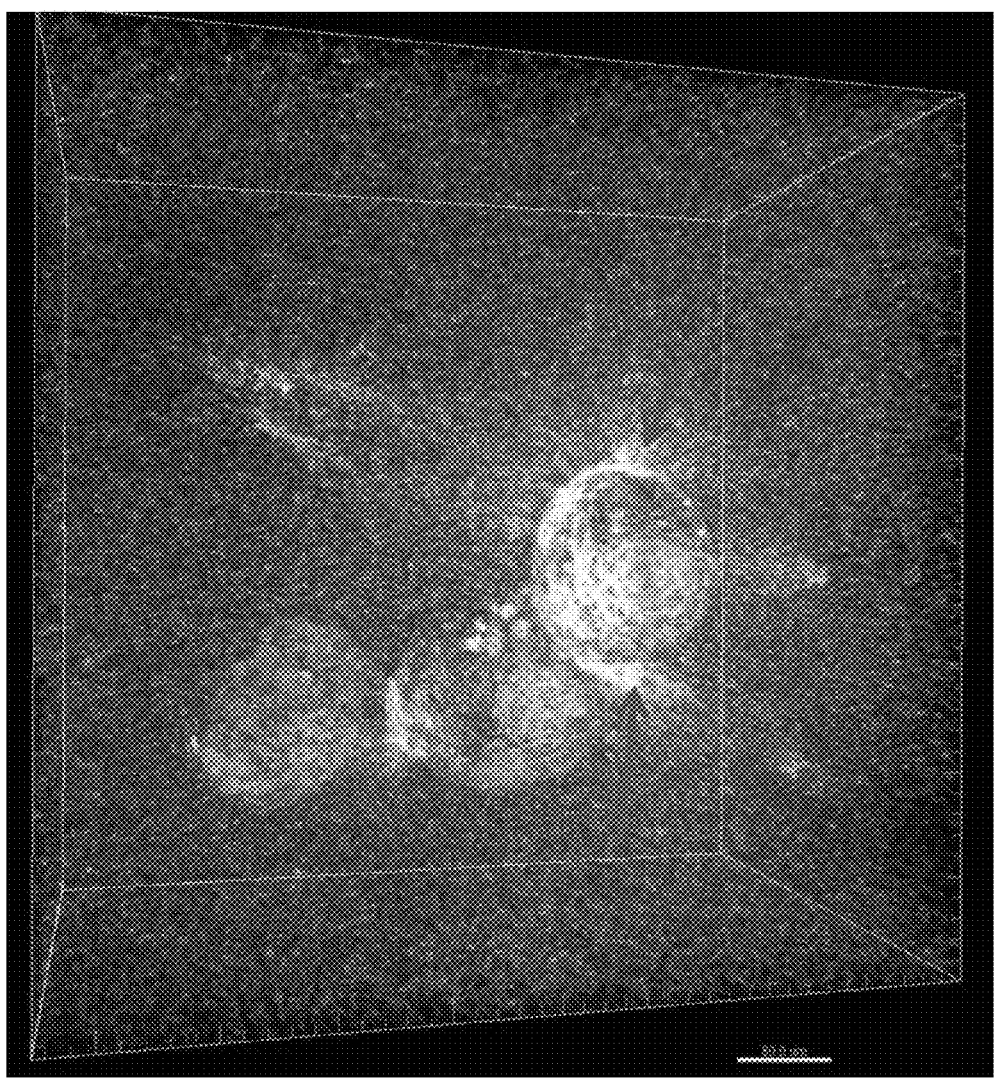
FIG. 6D is a 3D confocal reconstruction image of three Oct4-GFP mouse embryos embedded in a 3D stroma-collagen-endometrial matrix in which the embryo on the left has hatched from the ZP, but has not yet implanted into the stroma-collagen-endometrial matrix, the central embryo has hatched and is just started to embed as indicated by the aggregation of white collagen fibers, and the embryo on the right has hatched and has implanted as indicated by the dense white areas indicated by the red arrows indicating remodeling of the collagen fibers in the matrix, according to embodiments of the present invention.

FIG. 6D is a 3D confocal reconstruction image of three Oct4-GFP mouse embryos embedded in a 3D stroma-collagen-endometrial gel matrix, in which the embryo on the left has hatched from the ZP, but has not yet implanted into the stroma-collagen-endometrial matrix, the central embryo has hatched and is just starting to embed as indicated by the aggregation of white collagen fibers, and the embryo on the right has hatched and has implanted as indicated by the dense white areas with red arrows indicating the remodeling of the collagen fibers in the matrix.

Figure 7:
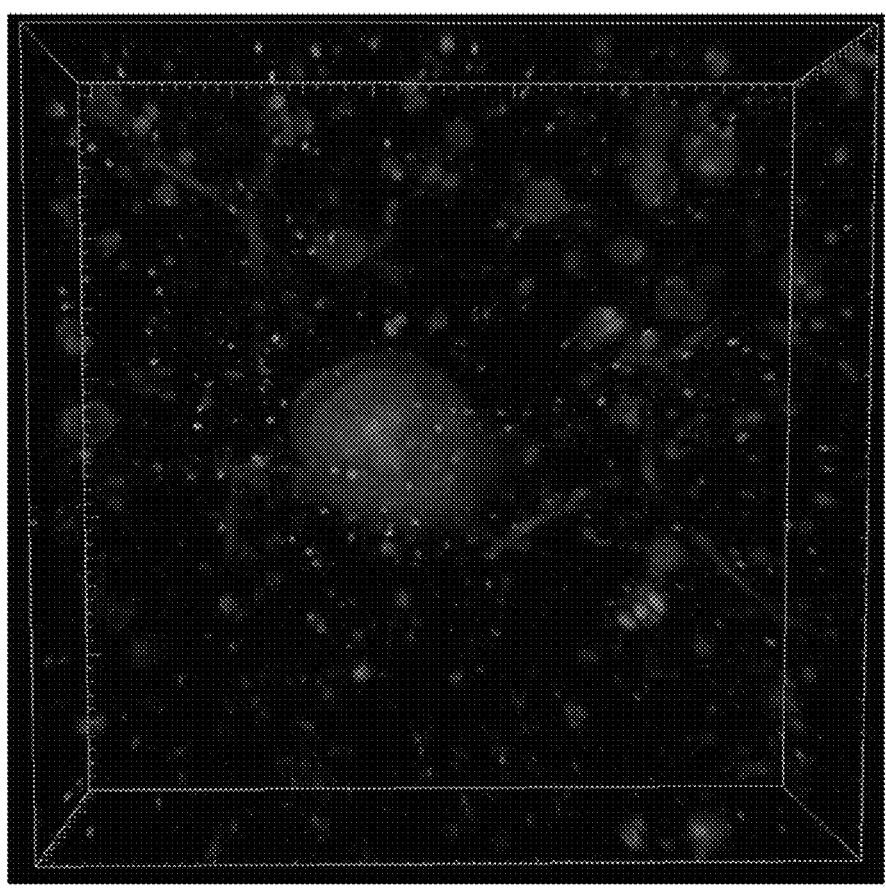
FIG. 7 is a 3D confocal reconstruction image of an Oct4-GFP mouse embryo embedded in a 3D stroma-collagen-endometrial matrix in which the embryo is surrounded by green stromal cells throughout the matrix; the stromal cells are green as they were harvested from the mother of the embryo; the ZP is stained with Alexa647-lectin as shown in purple and the cells of the embryo are green; the embryo is shown to be partially hatched from the ZP, according to embodiments of the present invention.

FIG. 7 is a 3D confocal reconstruction image of an Oct4-GFP mouse embryo embedded in a 3D stroma-collagen-endometrial matrix in which the embryo is surrounded by green stromal cells throughout the matrix. The stromal cells are green as they were harvested from the mother of the embryo. The ZP is stained with Alexa647-lectin as shown in purple, and the cells of the embryo are green. The embryo is shown to be partially hatched from the ZP.

Figure 8:
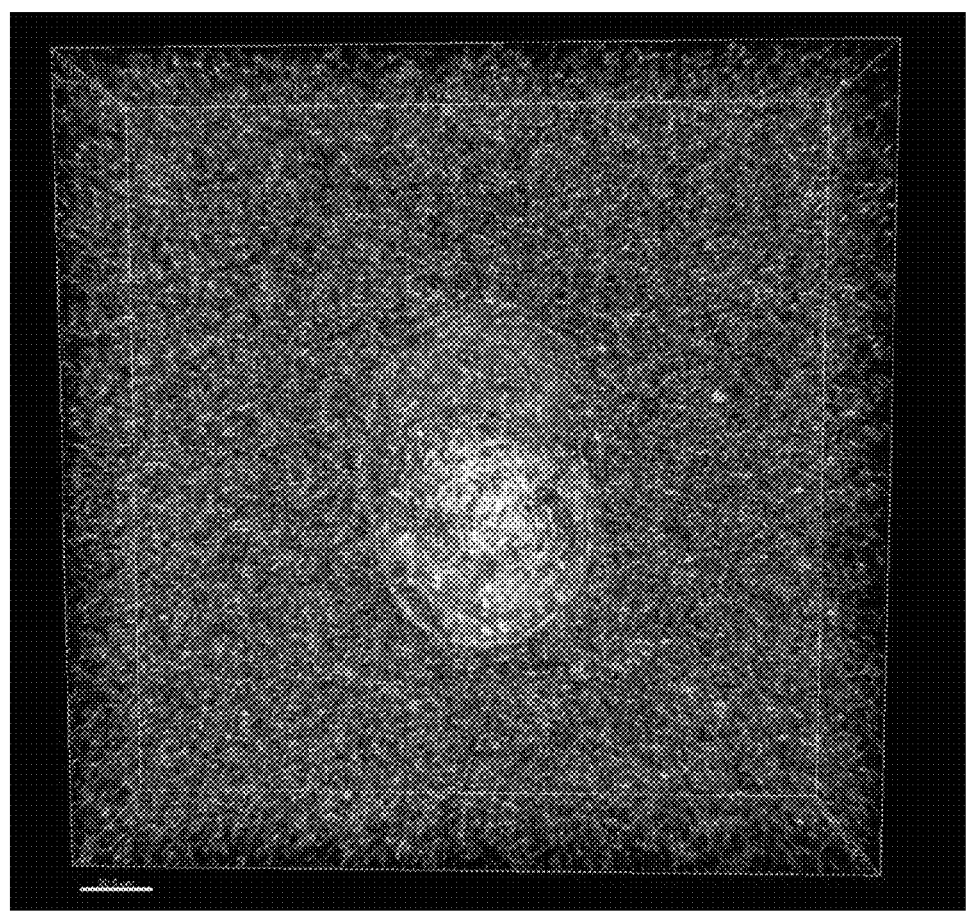
FIG. 8 is a 3D confocal reconstruction image of an Oct4-GFP mouse embryo embedded in a stroma-collagen-endometrial matrix; the embryo has hatched (absence of Alexa647 stained ZP) and implanted (white dense patch of collagen) into the matrix, and has started to elongate and adopt a bilateral symmetry indicative of the cylinder stage in embryogenesis, according to embodiments of the present invention.

FIG. 8 is a 3D confocal reconstruction image of an Oct4-GFP mouse embryo embedded in a stroma-collagen-endometrial matrix. The embryo has hatched (absence of Alexa647-stained ZP) and implanted (white dense patch of collagen) into the matrix, and has started to elongate and adopt a bilateral symmetry indicative of the cylinder stage in mammalian embryogenesis.

Some embryos cannot hatch out of the ZP by themselves. Some other embryos become amorphous colonies of cells after hatching, losing any kind of symmetry. It has been observed using the in vitro systems of embodiments of the present invention that the blastocyst comes out of the ZP by projecting a bleb, which immediately attaches to adjacent stromal or epithelial cells, when cells are provided, and helps the embryo to hatch from the ZP. Unhealthy embryos in arrested development never make it to the attachment stage. For this reason, the in vitro system and methods of the present invention may be used to discriminate healthy embryos by identifying embryos attached to the collagen/fibrin-uterine cell platforms.

Confocal microscopy in reflection mode reveals a very high level of detail without any labelling of the collagen fiber scaffold or any change in the spatio-temporal arrangement. As shown in FIGS. 6C and 6D, embryos attach to the matrix by pulling the collagen which leaves a characteristic and observable hallmark. The collagen surrounding the contact point of the embryo with the matrix results in a higher density of compacted fibers which are aligned towards the embryo. Therefore, visualization of the matrix conditions can provide direct evidence of the embryo health state and whether implantation has been initiated. The stage of implantation may also be inferred from matrix deformation level, and used for embryo screening.

In the range of 12 to 48 hours after hatching, cultured embryos are screened and those showing a healthy morphology (as described above) and that are attached to the matrix may be picked up for transfer into a uterus.

In some embodiments of the present invention, embryos are transferred upon reaching the implantation stage shown in FIG. 6D, lower right embryo. Alternatively, in some embodiments of the present invention, embryos are cultured in vitro until initial bilateral symmetry is reached.

Transfer of Implanted Embryo into Uterus:

Upon implantation of an embryo to a collagen or fibrin matrix in one of the in vitro systems according to embodiments of the present invention, the embryo is ready to be transplanted into the uterus for further in vivo development and birth. In some embodiments of the present invention, the in vitro complex, including a 2D or 3D collagen or fibrin matrix and the embryo therein, is transferred to the uterus. Embryo transfer techniques are known in the art, and any suitable method may be utilized with the modification that instead of an embryo alone, the embryo is transferred with its 2D or 3D collagen or fibrin complex.

For example, in some embodiments of the present invention, for a mouse embryo transfer, blastocysts were transferred to a day E2.5 pseudopregnant uterus of a mouse. The female was made receptive to implantation by mating with a vasectomized male. (See, for example, Cui et al., 2014, *J. Am. Assoc. Lab. Anim. Sci.*, 53:228-231 and Bermejo-Alvarez et al., 2014, *J. Vis. Exp.*, 28:e51214, the entire contents of both of which are herein incorporated by reference.)

In humans, the complex (which contains cell, matrix and implanted embryo), may be delivered to the mother using the current catheter based tools in combination with ultrasound imaging. It may be necessary to make a small incision in the endometrium to deliver the complex. (See, for example, Healy et al., 2015, *Semin. Reprod. Med.*, 33:83-91 and Porter, 2008, *Semin. Reprod. Med.*, 26:266-276, the entire contents of both of which are herein incorporated by reference.)

Buffers, Media and Supplements

For an example implantation assay, the embryos were incubated with the isolated epithelial and stromal cells in a matrix. The media that was used for implantation in vitro was DMEM/F12 with 10 mM HEPES and Penicillin and Streptomycin. The implantation complexes were incubated at 37° C. in 5% $CO_2$. The technique may also be carried out using available commercial media such as Vitrolife.

In some embodiments, the culture medium is supplemented with serum in a range of 10% to 50% by volume. In some embodiments, the culture medium is supplemented with 20% serum by volume.

Mouse blastocysts may be cultured longer when the medium is supplemented with rat serum (e.g., plasma). Human embryos may be cultured using umbilical cord blood serum. Alternatively, or additionally, human embryos may be cultured by supplementing the medium with human blood serum.

In vitro Kit

In some embodiments of the present invention, a kit for preparing an in vitro embryo system includes reagents in ready-to-use sterile form for harvesting uterine cells, preparing the collagen or fibrin matrices and embedding an embryo.

In some embodiments, the kit includes collagen or fibrinogen and trypsin. In some embodiments, the kit also includes serum. In some embodiments, the kit includes a collagen membrane (e.g., crosslinked collagen sheet). In some embodiments the kit includes fibrin and thrombin. In some embodiments, the kit includes media (e.g., DMEM/F12).

In some embodiments, the kit may include any one of the following alone or in combination:

Human sterile collagen 5-6 mg/ml type 1, 3, 4, and 5, 99% pure
plasma purified human fibrinogen 10-50 mg/ml 99% pure
plasma purified human thrombin 100 U/ml
0.05% trypsin
DNase 0.04%
Medium supplements: Human umbilical cord serum, adult plasma derived serum
DMEM/F12 50%50%
disposable, sterile 2 ml plastic tubes
HBSS sterile buffer
0.2 μm pore size mesh
Laparoscopic tools for embryo manipulation
NaOH 1M solution
10×PBS
Buffer for fibrinogen Buffer for Thrombin The kit may be complemented with different commercial media for embryo culture, such as the G-Series from Vitrolife. The rationale for this is that IVF clinics perform their protocols using their preferred media which, for their experience and observation, produces optimal results.

The following Examples are presented for illustrative purposes only, and do not limit the scope or content of the present application.

EXAMPLES

Example 1

The Isolation of Endometrial Cells

The endometrium is the epithelial layer that covers the lumen of the mammalian uterus. A mild enzymatic digestion with trypsin releases the endometrium from the uterine wall and disaggregates the cells into sheets of cells of about 50 to 200 cells/sheet. An example of isolation from mice is disclosed below. When using human tissue, a biopsy from the uterus is used following standard procedures, and the protocol will start at step 3.
1. Remove 1 or 2 uteri from 2-week-old mice.
2. Cut uteri open longitudinally.
3. Place uteri sample into 0.5% trypsin in HBBS (Hank's balanced salt solution) at 4° C. for 1 hour.
4. Leave the uteri sample and solution at room temperature for an additional hour.
5. Vortex the tubes for 10 seconds
6. At this point, the supernatant contains the epithelial cells. Transfer the supernatant to clean tubes.
7. Wash uteri twice with 5 ml HBSS to further remove epithelial cells and transfer the supernatant to the tubes from previous step.

Example 2

The Isolation of Stromal Cells

The decidua is the tissue from the uterus located underneath and adjacent to the endometrium. The stromal cells are released from the tissue by treating the uterus sample left after isolation of the epithelial (e.g., endometrial) cells, as described in the previous section. Trypsin treatment is carried out at higher temperature for stromal cells than the temperature for isolating epithelial cells, and DNase is also added to the incubation solution. The specific procedure is as follows:
1. Add 10 ml 0.05% trypsin+1 ml DNase 0.04% to the tissue sample
2. Briefly suspend the uterine fragments by pipetting medium up and down on top of them and place at 37° C. for 20 minutes.
3. Vortex for 10 seconds every 10 minutes for 20 minutes.
4. Transfer the supernatant (containing cells) to a new tube containing 1 ml of the relevant serum (i.e., rat, bovine, human).
5. Wash tissues with 5 ml HBSS and add the eluted liquid to the tube from the previous step.
6. Centrifuge cells 2000 rpm for 5 minutes in a table top centrifuge.
7. Resuspend the cells in 500 of DMEM/F12 medium (GIBCO®, Life Technologies) in 20% of the relevant serum.

The resuspended cells are ready to be counted and used for building the collagen or fibrin matrices.

Example 3

Blastocyst Isolation and Transfer to Matrix

Three to 4 week old mice were superovulated by the injection of 5 iu of pregnant mare's serum (PMS) intraperitoneally (IP) at 11 am, and 50 hours later with an IP injection of 5 iu (international units) human chorionic gonadotropin, and mated. The next morning, detection of the copulation plug confirmed pregnancy (E0.5). At E3.5, the mice were sacrificed and the blastocysts were flushed from the uterus with M2 medium (Sigma Aldrich). The uteri were transferred to enzyme medium for the isolation of epithelial and stroma cells. The blastocysts were placed in a 15 µl drop of KSOM medium (*Cold Spring Harbor Protoc* 2006, doi: 10.1101/pdb.rec10404). The drops were covered with sterile filtered mineral oil and incubated at 37° C. in 5% $CO_2$.

Human blastocysts may be obtained from IVF protocols at stage E3-E4.

For the implantation assay, the embryos were incubated with the isolated endometrial and/or stromal cells in a collagen or fibrin matrix. The media that was used for implantation in vitro was DMEM/F12 with 10 mM HEPES and Penicillin and Streptomycin. The implantation complexes were incubated at 37° C. in 5% $CO_2$.

Example 4

3D Stromal-Collagen Matrix Polymerization

1. Prepare 1-10 mg/ml collagen stock solution by diluting in DMEM/F-12 medium and neutralizing to pH=7.2-7.4 using sterile 0.1 M NaOH. Ready-to use collagen may also be used.
2. Count stromal cells and/or endometrial cells such that 10K to 200K cells of each cell type are placed in a 1.7 ml centrifuge tube.
3. Spin down cells using 2000 r.p.m. for 5 minutes
4. Remove supernatant and suspend cell pellet(s) with 20 µl of cold stock collagen solution (prepared in step 1). Mix gently by pipetting up and down avoiding bubbles.
5. Place the collagen-cell suspension on a cover-slip bottom culture dish.
6. Insert the embryos into the middle region of collagen-cell suspension using a mouth pipette or appropriate tool. Try not to place the embryos on the bottom of the collagen gel next to the glass surface.
7. Place the dish in the incubator at 37° C. for 30-45 minutes.
8. Add media to cover the collagen gel.

Example 5

3D Stromal-Fibrin Matrix Polymerization

1. Prepare fibrinogen solution in concentration of 1-15 mg/ml, and Thrombin solution in concentration of 1-20 U/ml using the appropriate buffers.
2. Count stromal cells and/or endometrial cells such that 10-200K cells are placed in a 1.7 ml centrifuge tube.
3. Spin down cells using 2000 r.p.m. for 5 minutes.
4. Take off the supernatant and suspend cell pellet with 5-20 µl of 1-20 U/ml Thrombin solution (made in step 1). Place it on a cover-slip bottom culture dish.

5. Take 10 μl of fibrinogen solution (made in step 1) and mix it with the thrombin-cell suspension. Pipette gently for 2 to 3 seconds trying to avoid bubbles.
6. Place the fibrinogen-thrombin-cell suspension on a coverslip bottom culture dish.
7. Without delay, insert the embryos into the middle region of fibrinogen-thrombin-cell suspension using a mouth pipette or appropriate tool. Try not to place the embryos on the bottom of the collagen gel next to the glass surface.
8. Place the dish in the incubator at 37° C. for 30-45 minutes.
9. Add media to cover the collagen gel.

Example 6

2D Collagen Matrix

1. Prepare 1-10 mg/ml collagen stock solution by diluting in DMEM/F-12 medium and neutralizing to PH=7.2-7.4 using sterile 0.1 M NaOH (or just use ready-to-use solutions). This solution can be stored at 4° C. for up to 3 months.
2. Count stromal cells such that 10K to 200K cells are placed in a 1.7 ml centrifuge tube.
3. Spin down cells at 2000 r.p.m. for 5 minutes using a table-top centrifuge
4. Take off the supernatant and suspend cell pellet with 5-20 μl of cold stock collagen solution (prepared in step 1). Mix gently by pipetting up and down avoiding bubbles.
5. Place the cell-collagen suspension in a 96-well and flatten the gel by gently shaking the dish.
6. Place the dish in the incubator for 30 minutes.
7. During the incubation period-count endothelial cells such that 5 amount of cells are placed in a 1.7 ml centrifuge tube.
8. Spin down the endothelial cells using 2000 rpm for 5 min.
9. Suspend the endothelial cell pellet with 100 μl of medium.
10. Once the incubation period of 30 min is over-pipette the endothelial cell suspension on the collagen-stromal cells complex.
11. Incubate the gel complex until the endothelial cells reach a spread and confluence morphology (incubation of several hours to overnight).
12. Place embryos on the epithelial-collagen complex and add media to cover the well.

Example 7

2D Fibrin Matrix

1. Prepare fibrinogen solution in concentration of 1-15 mg/ml, and Thrombin solution in concentration of 1-20 U/ml using the appropriate buffers.
2. Count stromal cells such that 10K to 200K cells are placed in a 1.7 ml centrifuge tube.
3. Spin down cells using 2000 r.p.m. for 5 minutes.
4. Take off the supernatant and suspend cell pellet with μl of Thrombin solution (made in step 1). Place the solution in a 96 well.
5. Take 10 μl of fibrinogen solution (made in step 1) and add it to the Thrombin-cell suspension. Pipette for 2 to 3 seconds while avoiding bubbles, and then flatten the gel by gently shaking the dish.
6. Place the dish in the incubator for 30 min.
7. During the incubation period count endothelial cells such that 10K to 200K cells are placed in a 1.7 ml centrifuge tube.
8. Spin down the endothelial cells using 2000 r.p.m. for 5 min.
9. Suspend the endothelial cell pellet with 100 μl medium.
10. Once the incubation period of 30 min is over-pipette the endothelial cell suspension into the fibrin-stromal cells complex.
11. Incubate the gel complex until the endothelial cells reach a spread and confluence morphology (several hours to overnight).
12. Place embryos on the epithelial-fibrin gel complex and add media to cover the well.

Example 8

Transgenic Mice

The embryos shown in the images were obtained from transgenic mice expressing fluorescent proteins. The Oct4-GFP line expresses the transcription factor Oct-4 fused to the green fluorescent protein in the nuclei and cytoplasm.

The strain Gt(ROSA)26Sor$^{tm4(ACTB-tdTomato,-EGFP)luo}$/J expresses the red fluorescent protein tdTomato in the membrane, as disclosed in Muzumdar et al., 2007, *Genesis*, 45:593-605, the entire contents of which are herein incorporated by reference. However, the disclosed in vitro system and methods according to embodiments of the present invention are compatible with standard, non-transgenic mammals.

Example 9

Imaging

Differential interference contrast microscopy (DIC) was used in FIGS. 2, 3, and 4. The images of FIGS. 1, and 5-8 were obtained by reconstruction of confocal optical slices using Imaris software. Argon 488 laser line was used to excite GFP, HeNe 561 and 647 was used to excite tdTomato and Alexa 647, respectively. The proper filters and prisms were set to obtain the final image on a Zeiss LSM-710 confocal microscope.

Reflection illumination was used in the confocal images of FIGS. 1, 5, 6A-6D, and 8. Reflection illumination was obtained by illuminating the sample with either the HeNe 561 or HeNe 647 and collecting the light in the same wavelength that was excited.

As disclosed throughout and evidenced by, for example, FIGS. 6C, 6D and 8, the in vitro systems and methods according to embodiments of the present invention, achieve initial implantation of the embryos to an in vitro matrix.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:
1. A method of identifying in vitro implantation of an isolated mammalian embryo derived from a donor uterus, the method comprising:
   adding the isolated mammalian embryo derived from the donor uterus at Carnegie Stage 2, 3, or 4 or an equivalent mammalian stage to a first suspension comprising collagen or fibrinogen to form a second suspension comprising the isolated mammalian embryo and the collagen or the fibrinogen;

polymerizing the second suspension to form a polymerized matrix comprising collagen fibers or fibrin fibers with the isolated mammalian embryo embedded therein; and observing or detecting remodeling or aggregation of the collagen fibers or the fibrin fibers in the polymerized matrix as an indication of in vitro implantation of the isolated mammalian embryo.

2. The method of claim 1, wherein when the first suspension comprises collagen, the polymerizing comprises incubating the second suspension at about 37° C., and when the first suspension comprises fibrinogen, the polymerizing comprises adding thrombin to the second suspension.

3. The method of claim 1, wherein the adding the isolated mammalian embryo and the polymerizing the second suspension occur concurrently.

4. The method of claim 1, further comprising:

adding endometrial cells and/or stromal cells from the donor uterus to the first suspension or the second suspension.

5. The method of claim 4, further comprising:

observing attachment of a bleb on the isolated mammalian embryo to the endometrial cells and/or the stromal cells.

6. The method of claim 1, further comprising adding a serum to the first suspension, the second suspension and/or the polymerized matrix.

7. The method of claim 6, wherein the serum is plasma-derived serum, human blood serum, and/or cord blood serum.

8. The method of claim 1, wherein the isolated mammalian embryo is from a human, a mouse, or a rat.

9. The method of identifying in vitro implantation according to claim 1, wherein the detecting comprises imaging the polymerized matrix using microscopy.

10. The method of identifying in vitro implantation according to claim 9, wherein the microscopy comprises reflection microscopy.

11. The method of identifying in vitro implantation according to claim 10, wherein the reflection microscopy comprises fluorescent microscopy and/or confocal microscopy.

12. The method of identifying in vitro implantation according to claim 9, wherein the imaging comprises two-dimensional imaging or three-dimensional imaging.

13. The method of identifying in vitro implantation according to claim 12, wherein the two-dimensional imaging is two-dimensional differential interference contrast (DIC) imaging and the three-dimensional imaging is three-dimensional confocal reconstruction imagine or three dimensional confocal imaging.

* * * * *

UNITED STATES PATENT AND TRADEMARK OFFICE
CERTIFICATE OF CORRECTION

PATENT NO. : 10,213,282 B2
APPLICATION NO. : 14/698839
DATED : February 26, 2019
INVENTOR(S) : Samuel Ojosnegros Martos et al.

It is certified that error appears in the above-identified patent and that said Letters Patent is hereby corrected as shown below:

On the Title Page

In Column 2, item (74),
Attorney, Agent, or Firm, Line 1    delete "Roce" and insert -- Roca --

In the Claims

In Column 16, Line 24, Claim 13    delete "imagine" and insert -- imaging --

In Column 16, Lines 24-25, Claim 13    delete "three dimensional" and insert -- three-dimensional --

Signed and Sealed this
Twenty-seventh Day of October, 2020

Andrei Iancu
*Director of the United States Patent and Trademark Office*